United States Patent [19]

Zwaneburg

[11] 4,111,970

[45] Sep. 5, 1978

[54] METHOD OF PRODUCING CHROMIUM (III)-N-ACYL-ANTHRANILATES

[75] Inventor: Dirk Jan Zwaneburg, Eindhoven, Netherlands

[73] Assignee: U.S. Philips Corporation, New York, N.Y.

[21] Appl. No.: 805,788

[22] Filed: Jun. 13, 1977

[30] Foreign Application Priority Data

Jun. 19, 1976 [DE] Fed. Rep. of Germany ....... 2627615

[51] Int. Cl.$^2$ ............................................. C01F 11/00
[52] U.S. Cl. ......................... 260/438.5 R; 252/62.1 L
[58] Field of Search ................................. 260/438.5 R; 252/62.1 L

[56] References Cited

U.S. PATENT DOCUMENTS

| 3,900,412 | 8/1975 | Kasel ............................... 252/62.1 L |
| 4,024,084 | 5/1977 | Sittardt et al. ............ 260/438.5 R X |

FOREIGN PATENT DOCUMENTS 2,116,556 10/1972 Fed. Rep. of Germany .... 260/438.5 R

*Primary Examiner*—Helen M. S. Sneed
*Attorney, Agent, or Firm*—Frank R. Trifari; Norman N. Spain

[57] ABSTRACT

The efficiency of chromium (III)-N-acylanthranilates as control materials for electrophotography is improved when a N-acyl-anthranilic acid is reacted in a methanolic solution, in the presence of sodium methanolate, with a chromium (III) salt, the resulting precipitate is dissolved in toluol and a part of the toluol is vacuum distilled.

2 Claims, No Drawings

METHOD OF PRODUCING CHROMIUM (III)-N-ACYL-ANTHRANILATES

BACKGROUND OF THE INVENTION

The invention relates to a method of producing chromium (III)-N-acylanthranilates for dispersions for applying solid particles to surfaces by electrophotographic means.

German application No. 24 60 763 discloses a dispersion for electrophotographically applying solid particles to surfaces, which dispersion comprises, besides the solid particles an apolar dispersion agent, a non-ionogenic macromolecular compound which is soluble in the dispersion agent and a charge-controlling material which controls charging of the solid particles. The dispersion comprises as the single charge-controlling material a chromium-(III) salt of the formula $Cr(AN)_n(OH)_{3-n}$, wherein $n = 1$, 2 or 3 and AN represents the residual acid of an anthranilic acid which may be substituted in the benzene nucleus, and whose amino group is acylated with a fatty acid of 6 to 20 carbon atoms, In the formula $n$ is preferably equal to 1 or 2. The acylated anthranilic acid may be substituted in the nucleus by halogen, aryl-, alkyl-aralkyl-, nitro-, amino-, O-alkyl-, O-aryl-, O-aralkyl-, hydroxyl-and/or ester groups. The amino group of the possibly substituted anthranilic acid is preferably acylated with a stearoyl group or a lauroyl group or an oleoyl group.

German application No. 21 16 556 discloses the preparation of chromium (III) salts of stearoyl anthranilic acids as, via a Schotten-Baumann condensation of anthranilic acid with stearoyl chloride to form stearoyl anthranilic acids. The sodium salt of these acids are converted in an aqueous solution with chromium (III) sulphate into chromium tris-stearoyl anthranilate, which is precipitated from the aqueous solution in the form of a green precipitate. After the usual washing and drying operation, the salt readily dissolves in hydrocarbon solvents. When used as control material in the above-mentioned dispersions the chromium (III)-N-acyl anthranilates produced in an aqueous solution have the disadvantage that the precipitate of the chromium compound is greatly contaminated with free acids (stearoyl anthranilic acid).

In accordance with German patent application 2460763 corresponding to U.S. Pat. No. 4,024,084 the chromium (III)-N-acyl anthranilates are produced in a methanol solution from N acyl anthranilic acids and $Cr(NO_3)_3 . 9H_2O$ in the required ratios by the addition of the methanolic solution of $CH_3ON$ methanol. The resulting precipitate is separated from the methanol by decanting, washed several times with methanol and dissolved again in toluene or chloroform or tetrahydrofuran. The solution is filtered and evaporated to dryness. The composition is checked by determining the chromium content. Standard solutions having a given concentration are produced for the production of the dispersions. Toluene, xylene, benzene, ethanol, propanol, butanol and other alcohols, dimethylformamide, dimethylsulphoxide, pyridine, acetonitrile, chloroform and other halogenized hydrocarbons may, for example, be used as solvents. The solvents may also contain small quantities of water.

A problem in the production of chromium (III)N-acylanthranilates is to produce the materials reproduceably in a simplest possible manner. It appeared, for example, that problems are encountered in the evaporation of toluene; there is a great difference in the properties of the chromium anthranilates obtained depending on the fact of whether the distillation of toluol has been done very thoroughly or not.

GENERAL DESCRIPTION OF THE INVENTION

It is an object of the invention to provide a method by means of which the chromium (III)-N-acyl anthranilates can be produced in such a form and with such reproduceable properties that these chromium compounds operate optimally as control materials in the above-mentioned dispersions.

In accordance with the invention, this object is accomplished in that the method of the above-described German application P 24 60763.4 is modified as follows: an N-acyl-anthranilic acid is reacted with a chromium (III)-salt in methanol in the presence of sodium methalonate, the precipitate obtained is dissolved in toluol, a part of the toluene, generally about 10%, is distilled off in vacuum and the remaining solution is adjusted, after filtration, with fresh toluene to the content of chromium (III)-N-acyl anthranilate required for the dispersion.

Thus one aspect of the invention involves the distillation of only about 10% of the toluene rather than all of it and the use of this toluene solution as a standard solution concentrate.

It is also advantageous to limit the quantity of solvent employed during the production of the chromium (III) compounds. However, N-stearoyl anthranilate dissolves very poorly in methanol at room temperature. A reduction of the quantity of solvent is obtained if the process is performed near the boiling point of the methanol. However, a problem then occurs in the precipitation of chromium (III)-N-stearoyl anthranilates, which is deposited as a cake on the bottom of the reaction vessel. It is therefore to be preferred to carry out the synthesis at room temperature and to limit the quantity of solvents at the same time.

In a preferred embodiment of the method according to the invention, carrying out the synthesis at room temperature and the limitation on the quantity of solvents employed is accomplished when the method is performed with the sodium salt of the N-stearoyl anthranilic acid. The solubility of the sodium salt of the N-stearoyl anthranilic acid in methanol is approximately 6 times as large as that of the anthranilic acid itself. As no precipitate of a chromium compound is produced (although a precipitate of $NaNO_3$ is produced) when mixing $Cr(NO_3)_3.9H_2O$ with 1 or 2 equivalents of $CH_3ON$ a in methanol the following synthesis is possible:

Solution I: 1 equivalent of N-stearoyl anthranilic acid with 1 equivalent $CH_3ONa$ in methanol;

Solution II: 1 equivalent of $Cr(NO_3)_3.9H_2O$ with 2 equivalents of $CH_3ON$ a in methanol. Solution I is added to solution II. During the reaction a precipitate of $CrAN(OH)_2$ occurs. The reaction can also be performed while introducing, slowly and drop-wise, the solutions I and II simultaneously into the reaction vessel. Also in this case a precipitate of $CrAN(OH)_2$ is produced. $Cr(AN)_2OH$ can be produced as follows:

Solution III: 2 equivalents of N-stearoyl anthranilic acid with two equivalents of $CH_3ONa$ in $CH_3OH$;

Solution IV: 1 equivalent of $Cr(NO_3)_3.9H_2O$ with 1 equivalent of $CH_3ONa$ in $CH_3OH$. Solution IV is slowly added dropwise to solution III. A precipitate of $Cr(AN)_2OH$ is produced.

The structure formulae given should not be regarded as a limitation. It is known that such and similar compounds form associates with a different number of monomers, including, possibly, also water can be stored. It is also possible that these compounds are present in the dispersions in a form which does not accuratley correspond with one of the above-mentioned stoichiometrical formulas. Therefore the formulas must only be regarded as approximate rations.

Among the advantages of the method according to the invention are a greater reproduceability of the chromium anthranilate thus produced and, consequently, a greater reproduceability in the production of dispersions for electrophotographic uses.

DETAILED DESCRIPTION OF THE INVENTION

The invention will be further explained with reference to the following embodiments.

EXAMPLE 1

504.5g (1.25 mol) of N-stearoyl anthranilic acid and 6.25 l methanol are heated, while being stirred mechanically, to the boiling point until everything has dissolved. Then a solution of 500.25g (1.25 mol) of $Cr(NO_3)_3.9H_2O$ in 1.25 l methanol is added. The solution thus obtained is mechanically stirred and heated to the boiling point. Thereafter, within approximately 15 minutes a solution of 3.75 mol of $CH_3ONa$ in a methanol is added. A green precipitate is then obtained which is deposited as a cake on the bottom of the flask. Stirring is continued for another hour and boiling is done with reflux. After cooling the supernatant solution is decanted. Thereafter the precipitate is washed twice with methanol (2.5 l) and then dissolved in toluene (6 l) at 40° C. The solution is filtered and subsequently subjected to a vacuum distillation until approximately 500 ml of the solvent has been distilled over. At the same time the residual methanol and water which, as a result of the synthesis are still present in the solution, are distilled off. Thereafter the solution is again filtered and replenished with toluene to 6.0 l. For the determination of the Cr-anthranilate content of the solution 25.0 ml of the green solution is evaporated to dryness in the rotary evaporator under vacuum. The flask is weighed prior to and after the process. The following solid matter was found: approximately 2.23 g in 25.0 ml. Yield: 535 g (87% of the theory of $CrAN(OH)_2$). The composition of the compound is determined by means of the chromium content. A chromium content of 9 to 12% was found which corresponds approximately to the formula $CrAN(OH)_2$. A standard solution with a given concentration can be simply produced from the concentrated toluol solution.

EXAMPLE 2

504.5y (1.25 mol) of N-stearoyl anthranilic acid is added to 6 l of methanol. A sodium methanolate solution which was produced from 28.75 g (1.25 mol) of sodium and 500 ml of methanol is added. All the materials are dissolved by stirring at room temperature (solution I). 500.25 g 1.25 mols) of $Cr(NO_3)_3.9H_2O$ is dissolved in 1.5 l of methanol (1.5 l) at room temperature and with mechanical stirring. A newly prepared sodium methylate solution (produced from 57.5 g (2.5 mol) of sodium and 1000 ml methanol) is slowly stirred into the solution. A white and a very small green precipitate are then obtained. The white precipitate is precipitated $NaNO_3$. The precipitates are allowed to settle, the supernatant solution is decanted, the green precipitate is dissolved with approximately 200 ml methanol and the two solutions are combined (solution II). Then solution I is slowly stirred dropwise into solution II. A green precipitate settles out. After the addition stirring is continued for another approximately 10 minutes and the supernatant methanol is decanted. The precipitate is washed with methanol and dissolved in toluene as in example 1.

EXAMPLE 3

80.4g (0.2 mols) of N-stearoyl anthranilic acid is dissolved in 600 ml of methanol and mixed with 0.2 mols of $NaOCH_3$ (0.2 mol) to form the Na-salt of the N-stearoyl anthranilic acid (solution III) 40.0g (0.1 mol) of $Cr(NO_3)_3.9H_2O$ is dissolved in 300 ml of methanol. Dissolved $CH_3ONa$ (0.1 mol) is slowly added dropwise. The resulting $NaNO_3$ precipitate is allowed to settle (solution IV). Then solution IV is stirred slowly dropwise into the solution III. A green precipitate settles down. After the reaction has finished, the supernatant methanol is decanted, the precipitate is washed twice with methanol, and the precipitate is then dissolved in 600 ml of toluene, filtered, 50 ml of the solution are distilled off and the solution is filtered again. The remaining volume is replenished with toluene to 600 ml. Thereafter the content is determined. Yield approximately 78 g (90%). Cr-content 6 to 6.7% which corresponds approximately with the formula $CrAN(OH)_2$.

What is claimed is:

1. A method of producing chromium (III)-N-acyl anthranilate dispersions for electrophotographically applying solid particles to surfaces, comprising reacting a N-acyl-anthranilic acid in a methanol solution in the presence of sodium methanolate with a chromium (III)-salt, dissolving the resulting precipitate in toluene, distilling off about 10% of the toluene in vacuum and adding sufficient fresh toluene to the remaining solution, after filtering, to provide the concentration of chromium (III)-N-acylanthranilate required for the dispersion.

2. A method as claimed in claim 1, wherein the N-acyl-anthranilic acid is converted into its sodium salt before the reaction with the chromium (III) salt.

* * * * *

UNITED STATES PATENT AND TRADEMARK OFFICE
CERTIFICATE OF CORRECTION

PATENT NO. : 4,111,970
DATED : September 5, 1978
INVENTOR(S) : DIRK JAN ZWANENBURG It is certified that error appears in the above-identified patent and that said Letters Patent are hereby corrected as shown below:

In the Title:

Change inventor's name from "Dirk Jan Zwaneburg" to

--Dirk Jan Zwanenburg--

Signed and Sealed this

Eighth Day of May 1979

[SEAL]

Attest:

RUTH C. MASON
Attesting Officer

DONALD W. BANNER
Commissioner of Patents and Trademarks